United States Patent [19]

Oeding et al.

[11] 4,226,764
[45] Oct. 7, 1980

[54] α-AMYLASE INHIBITOR FROM A STREPTOMYCETE AND PROCESS FOR ITS PREPARATION

[75] Inventors: Volker Oeding, Kelkheim; Werner Pfaff, Hofheim am Taunus; Laszlo Vertesy, Eppstein; Hans-Ludwig Weidenmüller, Hofheim am Taunus, all of Fed. Rep. of Germany

[73] Assignee: Hoechst Aktiengesellschaft, Frankfurt am Main, Fed. Rep. of Germany

[21] Appl. No.: 870,247

[22] Filed: Jan. 17, 1978

[30] Foreign Application Priority Data

Jan. 19, 1977 [DE] Fed. Rep. of Germany ....... 2701890

[51] Int. Cl.$^2$ ............................................. C07G 7/028
[52] U.S. Cl. ................................ 260/112 R; 424/177; 435/68; 435/886
[58] Field of Search .................... 260/112 R; 424/177; 195/80 R

[56] References Cited

U.S. PATENT DOCUMENTS

| 3,806,421 | 4/1974 | Ueda et al. .................. 260/112 R X |
| 3,855,066 | 12/1975 | Frommer et al. ................. 195/80 R |
| 3,876,766 | 4/1975 | Frommer et al. ............. 195/80 R X |

FOREIGN PATENT DOCUMENTS 1330230 9/1973 United Kingdom .
1496561 12/1977 United Kingdom .

OTHER PUBLICATIONS

Goto et al., *Chemical Abstracts*, vol. 83:176,706n (1975).

*Primary Examiner*—Walter C. Danison
*Attorney, Agent, or Firm*—Curtis, Morris & Safford

[57] ABSTRACT

Inhibitor for the glycoside hydrolases of the digestive tract, more particularly of the pancreatic α-amylase produced by fermentation of the specific microorganism *Streptomyces tendae*, strain 4158, as well as the variants and mutants thereof, the microbe strain per se and processes for the isolation of the inhibitor and for its purification.

1 Claim, 1 Drawing Figure

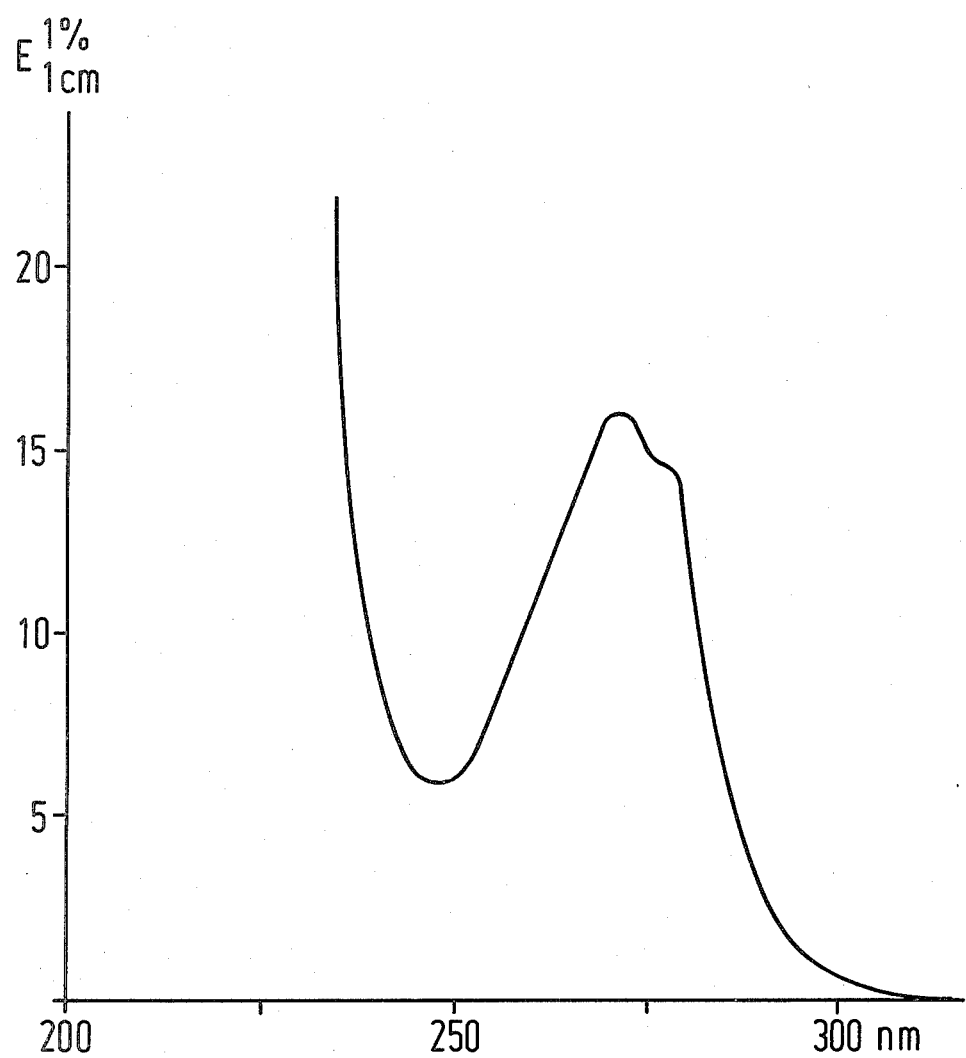

α-AMYLASE INHIBITOR FROM A STREPTOMYCETE AND PROCESS FOR ITS PREPARATION

This invention relates to a novel inhibitor of the glycoside hydrolases of the digestive tract, more particularly of the pancreatic α-amylase. The invention also relates to the preparation of such an inhibitor by fermentation of the specific microorganism *Streptomyces tendae*, strain 4158, as well as the variants and mutants thereof, the aforesaid microbe strain per se and to processes for the isolation of the inhibitor and for its purification.

Inhibitors of glycoside hydrolases from microorganisms, especially of actinomycetes, are known. Chemically, the substances hitherto investigated belong to the class of oligoor polysaccharides. Corresponding inhibitors probably having a peptide character have been reported to be unstable at elevated temperatures, capable of being inactivated more or less readily by trypsin, and above all to have a comparably lower activity.

There has now been found in the fermentation mixtures of *Streptomyces tendae*, strain 4158 a highly active inhibitor of pancreatic α-amylase which can be chemically classified among the peptides.

The inhibitor is characterized by a molecular weight of 5,000 to 10,000, an absorption maximum in the ultra-violet light at 279 nm, an isoelectric point of 4,4 and an amino acid composition as indicated below.

The inhibitor of the invention has a relatively high molecular weight. It does not diffuse or at most it diffuses to a very small extent only through commercial dialysis membranes, for example Visking ® hoses. It is, of course, difficult to determine the exact molecular weight and different methods give different results. The determination of the molecular weight in the analytical ultra-centrifuge (Biochemisches Taschenbuch, 2nd part, pages 746 to 767) yields values of approximately 10,000, whereas with the use of molecular sieves such as Sephadex ® G-50 super fine the determined molecular weight is 5,000 or even there below. Hence, as a result of the tests performed up to now, it can be assumed that the molecular weight is in the range of from 5,000 to 10,000.

The compound of the invention is a colorless substance which absorbs ultraviolet light with a maximum at 276 nm with a shoulder at 281 nm. $E_{1\ cm}^{1\%} = 16$. An absorption spectrum is shown on the annexed drawing.

According to its chemical structure the inhibitor is a peptide. It can be split into amino acids by hydrolysis. Up to now it has not been possible to detect other components besides amino acids. A determination of the amino acid composition by the method indicated by St. Moore and W. H. Stein (Methods in Enzymology, volume VI, pages 819 to 831, edited by Colovick and Kaplan in Academic Press, New York, London 1963) has the following result:

| aspartic acid | 5-6 | isoleucine | 1-2 |
|---|---|---|---|
| threonine | 5-6 | leucine | 3-4 |
| gerine | 3-5 | tyrosine | 4-5 |
| glutamic acid | 5-6 | phenylalanine | 0-2 |
| proline | 2-3 | histidine | 1-2 |
| alanine | 5-6 | lysine | 0-1 |
| glycine | 5-6 | arginine | 2-3 |
| cysteine | 3-4 | tryptophan | 1-2 |

-continued

| | |
|---|---|
| valine | 5-6 |

The value of tryptophan was estimated from the absorption of ultraviolet light. It is quite natural that the results of the amino acid analysis do not always point to an integral quantitative proportion and that measurements of this kind show certain errors. Therefore, the variation limits in the above enumeration do not indicate a non uniformity of the inhibitor but are a result of the unavoidable inaccuracy in measurement of the analysis method.

It is a characteristic feature of the inhibitor of the invention that a molecular proportion above average of the peptide is formed by the amino acids aspartic acid, glutamic acid, threonine, glycine, alanine and valine and that obviously the pure substance does not contain methionine. Owing to the fact that methionine is a widely spread amino acid, its substantial absence constitutes a good characteristic of identification of the inhibitor of the invention which may serve to determine the purity of the product especially in concentration processes.

The inhibitor of the invention has a positive reaction to peptide reagents and a negative reaction to phenol-sulfuric acid.

The α-amylase inhibitor of the invention is free from sugar and in this respect and by its amino acid composition, its molecular weight and its isoelectric point it differs from all known α-amylase inhibitors. Pure preparations of the inhibitor have an activity of 2 to 3 times $10^6$ AIU/g.

The claimed amylase inhibitor has a remarkable thermal stability for a substance with peptide nature. Even if it is boiled for one minute in a neutral or weakly acid medium (pH about 4 to 8), the glucoside-hydrolase inhibiting properties are not affected to a noteworthy extent.

As compared to other proteins, the inhibitor is inactivated by proteolysis very slowly only be pepsin, trypsin or chymotrypsin; therefore, during the period of therapeutic action a noteworthy reduction of the activity in the digestive tract is not to be expected.

The inhibitor is distinguished by a high specificity of action. The inhibition of pancreatic α-amylase is extremely high while bacterial α-amylase, for example those from *Bacillus subtilis* are not inhibited to a measurable degree. An effect on β-amylases has not been observed either.

A small dose of the amylase inhibitor of the invention ensures a complete inhibition of the enzymatic activity of pancreatic amylase. This result cannot be explained by the classic inhibition mechanisms in which the inhibition of the enzymatic catalysis depends on the relative quantitative proportion of inhibitor and substratum (starch). It could be assumed that an irreversible inactivation of the pancreatic amylase by the inhibitor of the invention takes place.

According to the invention the amylase inhibitor is prepared from the strain *Streptomyces tendae* 4158. This strain differs with respect to its spore morphology from the original strain S. tendae (Ettlinger et al., Arch.Microbiol 31, 351, (1959)). The spores are spherical with a diameter of 1 micron. The strain has the following properties:

| | |
|---|---|
| color of substrate mycelium | yellow brown; no change in |

| | -continued |
|---|---|
| color of the spored air mycelium | color by shifting of pH light grayish; redish brown according to ISCC methods of designating colors |
| morphology of spore chains spore morphology | Retinaculum apertum (RA) spherical spores with an average diameter of 1 μ, smooth to slightly verrucosic surface |
| melamine formation on peptone medium | positive |
| nitrate reduction | positive |
| substrate utlization spectrum | glucose + + arabinose + saccharose + xylose + inositol + + mannitol + + fructose + rhamnose + + raffinose + − cellulose − |

The strain *Streptomyces tendae* 4158 is deposited at the American Type Culture Collection (ATCC) under the registration number 31,210.

The fermentation can be carried out at 25° to 35° C., preferably 28° to 30° C., either immersed in a shake culture or in fermentation vessels of different dimensions, while stirring and aerating.

As culture medium a combination of sources of carbon and nitrogen proved to be especially suitable. A culture medium of this type contains, for example, besides the inorganic salts generally used in the culture of microorganisms, at least one carbon source, such as starch, glucose, cane sugar, fructose, lactose, glycerol, or molasses, and at least one nitrogen source such as soy flour, cornsteep liquor, yeast extract, cotton-seed flour, peanut flour, peptone, milk powder, nitrates or ammonium salts.

A culture medium having an optimum composition contains (% by weight in solution) 3 to 5% of soluble starch, 0.2 to 0.6% of cornsteep, 0.5 to 1.5% of glucose, 0.5 to 1% of $(NH_4)_2HPO_4$, 0.3 to 0.6% of soy flour, 0.5 to 1.5% of casein peptone. The amylase inhibitor is also obtained in a good yield on other starch-containing culture media, for example one containing 2 to 6% of peanut flour, 1 to 3% of potatoe starch, 3 to 5% of oat flour, 3 to 5% of wey powder, 1 to 2% of whey syrup, 1 to 2% of milk sugar, the choice of the nitrogen source and the buffer proportion not being very important as far as they remain within the physiological range. If, however, the content of starch is reduced or even completely omitted, the yield of inhibitor strongly diminishes. On the other hand, if the concentration of starch is substantially increased beyond 7%, an optimum supply of the microorganisms with oxygen is no longer ensured because of the high viscosity of the medium and the inhibitor decreases.

In the fermentation mixture the formation of the inhibitor generally starts between the tenth and thirtieth hour of fermentation and it is essentially terminated within the following 20 hours. Longer fermentation periods do not have an adverse effect on the inhibitor yield nor do they increase the yield to a noteworthy extent. Hence, it follows that the fermentation should be operated for about 30 to 70 hours.

For the isolation of the inhibitor the cell mass is removed from the fermentation solution by centrifugation, filtration or suction filtration as the preponderant proportion of the active ingredient is generally contained in the clear culture liquid.

If part of the inhibitor remains in the cell material owing to special fermentation conditions, it is by no means difficult to extract the active ingredient by a suitable method, for example by stirring with an organic solvent miscible with water, for example methanol, preferably with additional maceration of the cell material. The active substance dissolved in the extraction agent can be freed from the undissolved cell constituents by centrifugation or filtration and further treated in the same manner as the clear culture liquid.

The inhibitor can be isolated from the culture liquid by processes known in protein and peptide chemistry, for example by precipitation with organic solvents miscible with water such as acetone, isopropanol or other alcohols, or with salts, for example ammonium sulfate.

Alternatively, the inhibitor can be absorbed on appropriate carriers, for example active carbon, which are then separated from the aqueous solution by filtration or centrifugation. This can be done in a wide pH range of from 2 to 10, preferably 4 to 6. Ion exchangers may also be used for the separation of the α-amylase inhibitor of the invention. Since the claimed substance has acid as well as basic properties, i.e. is amphoteric, it can react with cation as well as with anion exchangers and can be removed from the fermentation solution with their help. To this end, all methods described in principle in the chapter dealing with ion exchangers in "Biochemisches Taschenbuch" published by H. M. Rauen, Springer Verlag 1964, 2nd part, pages 808 to 824 can be used.

During the working up of the fermentation mixtures it is often suitable to concentrate the culture liquid containing the substance of the invention by known methods of distillation, ultrafiltration, spray drying, lyophilization and the like. The inhibitor can then be separated from the concentrate in the manner described above. The concentrated culture filtrates can be enriched with the inhibitor by removing the essential impurities. To separate fatty constituents extractions with organic solvents proved to be suitable. By dialysis or optionally by ultrafiltration (C.J.O.R. and P. Morris "Separation Methods in Biochemistry" Ditman Publishing, London 1976, pages 944 to 950) the solution can be freed from low molecular weight substances. High molecular weight from low molecular weight substances. High molecular weight constituents such as nucleic acids, polysaccharides or some proteins can be removed by fractional precipitation, salting out or addition of a solvent miscible with water, for example acetone or a lower alcohol. In these cases the precipitant is added in an amount such that the readily precipitating constituents having a molecular weight above 100,000 are precipitated and the α-amylase inhibitor remains in solution. The enrichment steps described above can be combined in any order of succession and varied. In this manner, solutions highly enriched with inhibitor are obtained.

For final purification various appropriate processes can be used, for example gel and ion exchange chromatography or related techniques, the separating effect of which is not based exclusively on the principle of ion exchange, such as the separation with hydroxyl apatite. Further processes which may be used are solvent or salt precipitations, preparative electrophoresis and others. Especially good results are obtained with ion exchangers carrying diethylaminoethyl groups (DEAE) and by fractional precipitation with ammonium sulfate or ethanol whereby crystalline material may even be obtained.

The inhibitor according to the invention has interesting properties as therapeutic agent for the treatment of diabetes and prediabetes and adiposis and for the assistance of diet.

In human beings and animals starch-containing foodstuffs and luxury food raise the blood sugar level which results in an increased insulin secretion of the pancreas. The hyperglycaemia is caused by the splitting of the starch in the digestive tract under the action of amylase and maltase, whereby glucose is formed. With diabetics this hyperglycaemia is particularly pronounced and lasts for a long period of time. With people suffering from adiposity the increased insulin secretion acts on the lipogenesis and reduces the lipolysis.

Alimentary hyperglycaemia and hyperinsulinaemia after the ingestion of starch can be reduced by the amylase inhibitor of the invention, the effect being dependent on the dose. The amylase inhibitor of the invention can, therefore, be used as therapeutic agent in the treatment of diabetes, prediabetes and adiposity and to assist diet. To this end the substance is preferably given with the meals. The dose, which depends on the weight of the patient and the individual need, is in the range of from about 10,000 to 300,000 AIU, in special cases, however, it may be thereabove or below.

The amylase inhibitor of the invention is especially suitable for oral administration. It can be administered as pure substance or in the form of a pharmaceutical preparation together with the usual auxiliaries and carriers.

A combined administration together with other medicaments, for example blood sugar lowering or lipide lowering substances, may also be advantageous. Owing to the fact that high molecular weight peptides as such are not resorbed or resorbed to an insignificant extent only from the digestive tract, toxicological side effects of the substance of the invention are not to be expected. Considering the composition of amino acids, which is not unusual, possible proteolytic decomposition products are physiologically harmless. Consequently, with an oral administration of high doses of the amylase inhibitor to test animals no peculiar symptoms could be observed. When administered intraveneously to mice (1 g/kg) the inhibitor of the invention was found to have no noticeable toxic effect over an obervation period of 24 hours. To test the pharmacological effect of the amylase inhibitor, male Wistar rats having a weight of from 200 to 250 g were given on an empty stomach the inhibitor of the invention together with 2 g of starch per kilogram of body weight, immediately after having taken blood samples for the determination of the initial blood sugar value. Further blood samples were taken after 14 and 30 minutes and after 1, 2, 3 and 5 hours from the caudal vein. The blood sugar was determined in an autoanalizer by the method of Hoffman (J.Biol.-Chem. 120, page 51, (1937)).

NZO mice have a disordered glucose tolerance and, therefore, they are especially suitable for tests in which the blood glucose level is influenced. The test were carried out in the same manner as with rats. The blood was taken from the orbital vein plexus and the variation of the blood sugar content was determined over a period of 3 hours.

In analogous manner, the efficacy was tested in NMRI mice. In this case, too, the blood was taken from the orbital vein plexus and the blood sugar level was determined over a period of 3 hours.

Under the aforesaid test conditions, animals treated with the inhibitor of the invention exhibited a lower protracted increase in the blood sugar than untreated animals.

AMYLASE TEST

One amylase inhibitor unit (AIU) is the amount of inhibitor that can inhibit under the test conditions two amylase units (AU) by 50%. According to an international agreement, one amylase unit is the amount of enzyme splitting within 1 minute 1 microequivalent of glucosidic bonds in starch. The microequivalents of split glucosidic bounds are determined photometrically with dinitrosalicylic acid as microequivalents of reducing sugar. The results are calculated as micromols of maltose which are found with the aid of a calibrated straight line for maltose.

The test were carried out as follows:

α-Amylase from pig pancreas and the solution to be tested were incubated together for 10 to 20 minutes at 37° C. in 1.0 ml of 20 mmol per liter of phosphate buffer of pH 6.9 and 10 mmols per liter of NaCl. The enzymatic reaction was started by adding 1.0 ml of soluble starch (0.25% in the specified buffer) according to Zulkowski. After 10 minutes exactly, the reaction was stopped by adding 2.0 ml of dinitrosalicylic acid color reagent (according to Messrs. Boehringer, Mannheim; Biochemical information II) and heated for 5 minutes in a boiling water bath for color development. After cooling, the extinction was measured at 546 nm against the reagent alone. The 50% inhibition with varrying amounts of inhibitor was determined graphically by probability plotting against the non inhibited enzyme reaction.

The following examples illustrate the invention.

EXAMPLE 1

The strain *Streptomyces tendae* 4158 was inoculated on a culture medium consisting of 50 g of oat flakes
1,000 ml of $H_2O$, $pH_A$ 7.2 in slant tubes. The inocculated tubes were incubated for 7 days at 30° C. and then kept at +4° C. The spores were washed off with 10 ml of sterilized distilled water or physiological NaCl solution. 1.0 ml of the suspension was then used to inoculate a 300 ml Erlenmeyer flask containing 35 ml of sterilized nutrient solution having a pH of 7.7 and containing 1% of glucose
1% of soy fluor
0.25% of NaCl, pH 7.7

The flask was shaken for 48 hours at +30° C. at 220 revolutions per minute at a amplitude of 4 cm. 5 ml each of the preculture were transferred into Erylenmeyer flasks each containing 35 ml of sterilized nutrient solution having a pH of 8.3. The main culture contained 4% of starch
0.4% of cornsteep liquor
1.0% of glucose
0.8% of $(NH_4)_2HPO_4$
0.4% of soy flour
1.0% of peptone, $pH_A$ 8.3

The main cultures were also shaken for 2 to 3 days at +30° C. at 220 revolutions per minute on a shaking machine at an amplitude of 4 cm. The content of α-amylase inhibitor was determined on the first, second and third day according to the test prescription.

The strain Streptomyces tendae 4158 yielded under the aforesaid test and culture conditions 100 AIU/ml on the average at a final pH of 5.2.

EXAMPLE 2

The conditions were the same as in Example 1 with the exception that for the main culture a fermentation vessel having a total volume of 300 liters was used which contained 200 liters of a sterilized nutrient solution containing 4% of starch
0.4% of cornsteep liquor
1.0% of glucose
0.8% of $(NH_4)_2HPO_4$
1.0% of casein peptone
0.1% of desmophen, $pH_A$ 8.3–8.5

The mixture was sterilized for 45 minutes at 121° C. and 1 bar. The glucose was sterilized separately and added after cooling the fermenter to operation temperature.

After sterilization the pH should amount to 6.8. If necessary, it can be adjusted by sterilized acid (2 N $H_3PO_4$) or alkali (2 N NaOH). The main stage was inoculated with 20 l, corresponding to 10%, of a preculture prepared as described in Example 1 in a small fermenter having a total volume of 30 liters.

Fermentation was carried out at 30° C. for 50 to 70 hours. The mixture was aerated with 6 m³/hr while stirred at 250 revolutions per minute under an excess pressure of 0.3 bar.

The course of fermentation as regards inhibitor activity, substratum decomposition, development of single cell protein and physical properties of the culture solution (surface tension, viscosity, density, osmotic pressure) was controlled by taking samples.

The maximum inhibitor activity was reached after 60 hours of cultivation with 105 AIU/ml on the average. Thereafter, the contents of the fermenter were worked up.

EXAMPLE 3

The conditions were the same as in Examples 1 and 2 with the exception that for the main stage a bioreactor having a total volume of 4,000 liters was used which was charged with 2,500 liters of nutrient solution containing 6% of starch
1.0% of glucose
0.4% of cornsteep liquor
0.8% of $(NH_4)_2HPO_4$
1.0% of soy peptone
0.1% of desmophen, $pH_A$ 7.0–7.3

The mixture was sterilized for 60 minutes at 121° C. and 1 bar. The glucose was sterilized separately and added by pumping under sterile conditions after cooling of the fermenter to operating conditions.

If necessary, the pH was adjusted to an initial value of 7.0 to 7.3 by adding sterile acid ($H_3PO_4$) or alkali (NaOH).

The solution was inoculated with 200 liters of a preculture prepared as described in Example 2.

Fermentation was carried out for 70 hours at a temperature of 30° C., an aeration of 60 Nm³/hr, an excess pressure of 0.5 bar and while stirring with 180 revolutions per minute.

All important process, organism and activity data were controlled during the entire fermentation period by taking samples as described in Example 2.

After a fermentation period of 70 hours, an average activity concentration of 95 AIU/ml was reached, whereupon the fermentation was interrupted and the culture solution worked up.

EXAMPLE 4

10 Liters of a filtered culture fluid having an activity of 100 AIU/ml was dried in a spray drier whereby 400 g of a light brown powder was obtained. For the removal of fats the powder was thoroughly stirred with a mixture of 1 l of methanol and 1 l of chloroform and filtered off with suction. The undissolved product still moist with solvent and containing the active substance was dissolved in 3 l of water, adjusted to pH 6.5 and mixed with 4.5 l of methanol. A light flocculent precipitate was formed which was removed by centrifugation and rejected as it only contained negligible amounts of the α-amylase inhibitor. The dark supernatant of the methanol precipitation which contained the desired inhibitor was freed from methanol under reduced pressure and the solution concentrated to a volume of 2.5 liters was dialyzed against distilled water until it was free from salt. The tenate contained 9 g of dry matter (specific activity 96 AIU/mg). At pH 5.5 the tenate was saturated to 50% by ammonium sulfate, 79 g thereof being necessary for 250 ml. By salting out a precipitate was obtained containing about 90% of the active substance. After centrifugation, the supernatant was rejected and the precipitate dissolved again in distilled water. At pH 8 ammonium sulfate was again added, this time to a saturation of 15% and, after removal of the precipitate a further amount to obtain a 35% saturation. The precipitate formed by salting out between the concentrations of 15 and 35% contained the main quantity of the amylase inhibitor. The fractional precipitation was repeated.

After dialysis and drying, 360 mg of a product having a specific activity of 992 AIU/mg were obtained. 350 mg of the crude substance were separated and enriched in Sephadex$^{(R)}$G-50 fine in a glass column 100 cm long having a capacity of 1.2 liters, using as swelling and eluting agent aqueous 5 millimolar phosphate buffer solution of pH 8 to which 0.02% of sodium azide had been added. The crude product was dissolved in 15 ml of the specified buffer and charged to the column. Elution was carried out over a period of 2 days while collecting 15 ml fractions. The 4 most active fractions were collected, dialyzed until they were free from salt and lyophilized. 60 mg of a white powder having an activity of 2520 α-amylase inhibitor units per milligram.

EXAMPLE 5

2,200 l of culture liquid were cooled to 6° C., 2% of kieselguhr were added and the whole was filtered through a chamber filter press. The filter cake (about 450 kg moist) was discharged and the clear filtrate (1750 l having an activity of 95 AIU/ml) was concentrated to 120 liters, after the addition of 500 g of sodium azide, in a downdraft evaporator. The concentrate obtained was cooled to 1° C. and 120 l of cooled acetone were slowly added while stirring. To complete precipitation stirring was continued for 15 minutes, 1 kg of kieselguhr were added and, for clarification, the whole was passed through a Schenk press. The solid containing the filter aid was discarded. The acetonic filtrate containing the active substance was mixed with 380 l of acetone while stirring and cooling whereby an acetonic suspension of about 80% strength was obtained. The formed (second) precipitate contained the desired amylase inhibitor. To isolate the inhibitor, the suspension was abandoned without stirring, whereupon the precipitate settled so that the supernatant could be siphoned off. From the supernatant of the second acetone precipitation small amounts of precipitate could be separated by centrifugation. This solid matter was dissolved at pH 7 and the solution was added to the solution of the precipitate (cf. below). The main amount of precipitate remaining in the precipitation vessel was dissolved in 120 l of water at pH 7 and the solution formed was clarified in a flow centrifuge (Cepa$^{(R)}$ 1,700 rev. per minute). In this manner 90 g of inactive suspended particles were removed. In a DDS ultrafiltration device (membrane no. 800) the clear water phase was concentrated to 15 liters and dialyzed. To ensure the complete removal of salts the tenate was diluted with distilled water and concentrated again. After having repeated this procedure 2 to 3 times the tenate containing the amylase inhibitor was practically free from salt. Next, the inhibitor was precipitated at pH 5.5 by adding 19.5 kg of ammonium sulfate to 50 liters tenate solution, the precipitate was separated by centrifugation and the supernatant discarded. The precipitate was again dissolved in 40 l of water and reprecipitated at pH 7.5 with 12.5 kg of ammonium sulfate. After separation of the clear phase in a tube centrifuge, the precipitate was reprecipitated in fractions as described in Example 4.

3.2 kg of ammonium sulfate were added to 40 l of the solution of the redissolved substance of pH 5.5 whereby an inactive precipitate was formed which was separated and rejected. By further concentrating the liquid phase by the addition of 7.4 kg of ammonium sulfate the main portion of the active substance was then separated from the liquid phase. The precipitates were collected and dialyzed against distilled water and lyophilized. 114 g of a brown powder were obtained having an activity of 1,100 AIU/mg.

For further purification a glass column having a diameter of 5 cm and a height of 50 cm (volume about 1 liter) was charged with DEAE-Sephadex A-25$^{(R)}$ which had been equilibrated previously to pH 7.5 with 1/30 molar phosphate buffer and 0.02% sodium azide. The column was then charged with 10 g of the substance dissolved in 100 ml of the same buffer. The column was first eluted with 1 liter of the buffer and then sodium chloride was gradually added at a rate to ensure a continuous gradient. The effluent of the column was collected in fractions, the fractions having an NaCl concentration of about 0.5 mol containing the amylase inhibitor. These fractions were collected and dialyzed against distilled water. By lyophilization 5.6 g of a light brown substance were obtained having an activity of 2,200 AIU/mg.

When subjected to a gel chromatographic purification as described in Example 5, the 5.6 g of material gave 4.1 g of a colorless powder having an activity of 2,800 AIU/mg. After a 20 hour hydrolysis in hydrochloric acid in a Beckmann Multichrome analyzer, the following composition of aminoacids was found:

| | |
|---|---|
| Aspartic acid | 7.72% |
| Threonine | 7.66% |
| Serine | 5.35% |
| Glutamic acid | 10.05% |
| Proline | 3.43% |
| Glycine | 4.93% |
| Alanine | 5.84% |
| ½ Cysteine | 4.26% |
| Valine | 7.72% |
| Methionine | 0.41% |
| Isoleucine | 2.30% |
| Leucine | 5.18% |
| Tyrosine | 10.24% |
| Phenylalanine | 3.35% |
| Histidine | 3.01% |
| Lysine | 1.45% |
| Arginine | 5.16% |

What is claimed is:

1. Peptidic glycoside hydrolase inhibitor obtained by cultivating Streptomyces tendae 4158 (ATCC no. 31210) and isolating the inhibitor from the culture, said inhibitor having a molecular weight in the range of from 5,000 to 10,000, an absorption maximum in the ultraviolet light at 276 nm, an isoelectric point of 4.4 and the following amino acid composition:

| | | | |
|---|---|---|---|
| aspartic acid | 5–6 | glycine | 5–6 |
| threonine | 5–6 | alanine | 5–6 |
| serine | 3–5 | cysteine | 3–4 |
| glutamic acid | 5–6 | valine | 5–6 |
| proline | 2–3 | isoleucine | 1–2 |
| leucine | 3–4 | lysine | 0–1 |
| tyrosine | 4–5 | arginine | 2–3 |
| phenylalanine | 0–2 | tryptophan | 1–2 |
| histidine | 1–2 | | |

* * * * *